United States Patent [19]

Higuchi et al.

[11] 4,085,214

[45] Apr. 18, 1978

[54] STABLE PRO-DRUG FORMS OF THEOPHYLLINE

[75] Inventors: Takeru Higuchi; Nicolae S. Bodor; Yu-Neng Kuo, all of Lawrence, Kans.

[73] Assignee: INTERx Research Corporation, Lawrence, Kans.

[21] Appl. No.: 732,979

[22] Filed: Oct. 18, 1976

[51] Int. Cl.² .................... A61K 31/52; C07D 473/08
[52] U.S. Cl. ..................................... 424/253; 260/256
[58] Field of Search ........... 424/253; 260/256, 240 G, 260/240 K

[56] References Cited
U.S. PATENT DOCUMENTS

| | | | |
|---|---|---|---|
| 2,729,643 | 1/1956 | Stoll et al. | 260/256 |
| 3,737,433 | 6/1973 | Mohler et al. | 260/256 |
| 3,813,394 | 5/1974 | Tensho et al. | 260/252 |
| 3,935,196 | 1/1976 | Higuchi et al. | 260/240 J |

Primary Examiner—Leonard Schenkman
Attorney, Agent, or Firm—Bacon & Thomas

[57] ABSTRACT

There is provided exceptionally stable and useful pro-drug forms of theophylline having the formula:

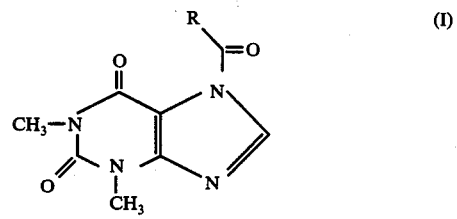

wherein R represents a straight or branched phenylalkenyl group having 2-8 carbon atoms in the alkenyl portion.

The compounds of this invention are useful in the treatment of asthma in warm-blooded animals. Upon administration, the compounds of this invention slowly go into solution and subsequently cleave prior to and/or during the absorption process, releasing theophylline in a sustained manner at a non-toxic, therapeutic level; that is, without the large blood level variations normally observed when theophylline per se is administered.

8 Claims, No Drawings

STABLE PRO-DRUG FORMS OF THEOPHYLLINE

BACKGROUND OF THE INVENTION

1. Field of the Invention

The present invention is directed to novel and useful derivatives of theophylline, a known drug useful in the treatment of asthma. More particularly, the present invention is directed to certain stable "pro-drug" forms of theophylline useful in the treatment of asthma in warm-blooded animals, e.g. humans.

For the purposes of this application, the term "pro-drug" denotes a stable derivative of a known and proven prior art compound (i.e., theophylline) which derivative, when administered to a warm-blooded animal, "cleaves" in such a manner as to release the proven drug form and permit the same to attain a sustained therapeutic level for a longer period of time than that which could be attained if the proven drug form per se was administered. More specifically, because of the very low water solubility and low dissolution rate of the pro-drug forms of this invention, such forms enable theophylline to be released quite slowly thus permitting therapeutic blood levels of the same to be maintained over an extended period of time, while at the same time, avoiding non-toxic blood levels of theophylline to be reached. The pro-drug forms of this invention are cleaved so rapidly in aqueous solution that the "pro-drug" form per se does not reach the bloodstream, but rather, cleavage of the pro-drug occurs before and/or during the absorption process. As such, substantial and sustained bioavailability is assured.

2. Description of the Prior Art

Theophylline, normally administered as the ethylenediamine salt (Aminophylline) or choline salt, is a useful and potent bronchodilator commonly prescribed for the treatment of bronchial asthma. Because it is readily soluble, Aminophylline has for many years been accepted as an effective bronchodilator when given orally. However, Aminophylline in solution becomes highly alkaline and is hydrolized by the gastric juice with resultant gastric irritation from the free theophylline liberated.

5 to 12 mcg./ml of whole blood or 10 to 25 mcg./ml of plasma are the relative blood levels of theophylline generally accepted as necessary to achieve effective bronchodilation. See E. G. Truitt, V. A. McKusick, J. C. Krantz, Jr.; *Pharm. Exp. Ther.*, 100, 309 (1950) and M. Warwick Turner; *Brit. Med. Jr.*, 2, 67 (1957), respectively. These theophylline blood levels are, however, difficult to attain, since as a result of the gastrointestinal upset experienced, patients cannot tolerate an adequate therapeutic dose of the drug. Reports in the literature with a variety of theophylline derivatives have often shown not only that theophylline blood levels achieved are below the values required for the relief of a brochospasm, but also that even when these therapeutic levels are obtained, they fall off extremely rapidly in the first few hours following administration of the drug. Thus, repeated dosing of the patient about every 3 to 4 hours is necessary. See E. G. Truitt, V. A. McKusick, J. C. Krantz, Jr., and Mr. Turner-Warwick, and R. H. Jackson, J. I. McHenry, S. B. Moreland, W. J. Raymer, and R. L. Etter; *Dis. Chest.*, 45, 75 (1964) and J. Schluger, J. T. McGuinn, and D. J. Hennesey; *Amer. J. Med. Sci.*, 233, 296 (1957), respectively.

In addition, even when therapeutic blood levels of theophylline are achieved, the amount of theophylline administered to a patient is so excessive that the therapeutic blood level achieved approaches and often reaches toxicity.

In one attempt to overcome the above disadvantages associated with administering theophylline, certain individuals have prepared a continuous-release formulation, such that the release rate of theophylline is dependent upon the formulation medium into which it is incorporated. That is, sustained therapeutic blood levels of theophylline are achieved through the use of a particular pharmaceutical formulation rather than chemical modification of the theophylline molecule. See, C. Boroda, R. B. Miller, S. T. Leslie, E. G. Nicol and I. Thompson; *Clin. Pharm.*, 383 (1973) and D. McIntosh, *Brit. J. Clin. Pharm.*, 12, 233 (1971) respectively.

Some theophylline derivatives, analogous to the compounds of formula (I) described hereinabove, have been prepared and described in the literature for the purpose of studying their chemistry per se, without any indication of any pharmaceutical utility. For instance, 7-acetyltheophylline was reported in three different articles. See, for instance, T. Higuchi, H. K. Lee and Ian H. Pittman; *Farm. Aikak.*, 80, 55 (1971) and Y. Ishido, A. Hosono, S. Isome, A. Maruyama, and T. Sato; *Bull. Chem. Soc. Japan*, 37, 1389 (1964), respectively.

7-acetyltheophylline and 7-benzoyltheophylline were reported in H. Biltz, and K. Struffe, *Ann.*, 404, 170 (1914) as well.

7-propionyltheophylline and 7-butyryltheophylline have also been reported in the literature. See, Y. Ishido, A. Hosono, S. Isome, A. Maruyama, and T. Sato, supra.

U.S. Pat. No. 2,729,643 discloses certain 7-carboxamidotheophylline derivatives useful as diuretics.

Finally, U.S. Pat. No. 3,935,196 assigned to the present assignee of record discloses a number of pro-drug forms of theophylline. However, these forms are highly unstable and greatly impede efforts to formulate. That is, due to the instability of the pro-drug molecule per se, shelf life of the final formulated product is dramatically diminished. Additionally, this instability factor also precludes achievement of suitable sustained blood levels of theophylline following prolonged shelf life. Pending U.S. patent application Ser. No. 526,219, filed Nov. 22, 1974, now U.S. Pat. No. 4,000,132 also discloses a process for preparing the pro-theophylline compounds of the above identified U.S. Pat. No. 3,935,196 in a more stable form than previously existed. However, even though increased stability is attained, such is insufficient from a commercial standpoint. That is, formulation of these enhanced stable forms for commercial purposes leads to rapid degradation of the pro-theophylline derivative such that its utility is totally impractical.

SUMMARY OF THE INVENTION

It is one object of the present invention to provide novel, useful but more importantly, stable pro-drug forms of theophylline, useful in the treatment of bronchial asthma in warm-blooded animals, e.g. humans.

It is another object of the present invention to provide novel, useful and stable pro-drug forms of theophylline which cleave in such a manner as to enable the original proven drug form (theophylline) to be released when administered to a warm-blooded animal at a slow, but continual, non-toxic therapeutic level and to further permit the cleaved moiety (ies) unassociated with the proven drug form to be excreted without absorption or metabolized in a non-toxic fashion.

Still, it is another object of the present invention to provide novel, useful and stable pro-drug forms of theophylline which because of their ability to cleave before and/or durin the absorption process insure that substantial and sustained theophylline bioavailability as set forth above is attained.

Finally, it is an object of the present invention to provide normal, useful and stable pro-drug forms of theophylline as described above which owing to their exceptional stability will enjoy sustained shelf life over their prior art pro-drug forms.

Accordingly, all of the above objects are satisfied when employing a pro-drug of theophylline, having the formula I set out below:

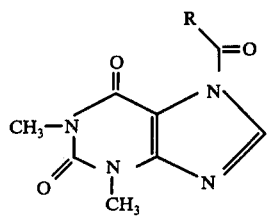

wherein R represent a straight or branched phenylalkenyl group having 2–8 carbon atoms in the alkenyl portion.

In regard to the above generic formula, when substituent "R" represents a straight or branched $C_2$–$C_8$ alkenylphenyl group, the $C_2$ alkenylphenyl (cinnamyl) moiety is most preferred.

While all the compounds within the present invention satisfy the objectives noted above, certain compounds are preferred as set forth below:

(1) 7-(3-phenyl-propenoyl)-theophylline
(2) 7-(6-phenyl-hexen-2-oyl)-theophylline
(3) 7-(8-phenyl-octen-5-oyl)-theophylline Most preferred, however, is the 7-(3-phenyl-propenoyl)[cinnamyl]-theophylline derivative.

DETAILED DESCRIPTION OF THE INVENTION

The compounds of the present invention are easily prepared by introducing the appropriate "R" moiety into either reaction scheme disclosed in U.S. Pat. No. 3,935,196 or applicant's pending patent application, Ser. No. 526,219, filed Nov. 22, 1974, the subject matter of both of which is incorporated herein by reference.

Without further elaboration, it is believed that one of ordinary skill in the art can, using the proceeding description, utilize the present invention to its fullest extent. The following specific embodiments are, therefore, to be construed as merely illustrative, and not limitative of the remainder of the specification and claims in any way whatsoever.

EXAMPLE 1

COMPARATIVE STABILITY STUDY

In order to demonstrate the unexpected stability observed with the compounds of formula (I) versus those of the prior art, the following comparison between 7-(3-phenyl-propenoyl)-theophylline (this invention) and 7,7'-succinylditheophylline (U.S. Pat. No. 3,935,196) was made. The former compound was prepared by synthesis scheme (I) below. Optionally, synthesis scheme (II) is available. 7,7'-succinylditheophylline was prepared in accordance with Example II of applicant's pending Ser. No. 526,219 application noted earlier.

(I) To a 3-neck, 3-liter flask equipped with a dropping funnel, concenser and mechanical motor stirrer, N,N-dimethylformamide (25 ml, 0.34 moles) was added. Then, 250 ml (0.315 mole) of $COCl_2$ (12.5% in Benzene, $CH_2Cl_2$ or toluene) was added slowly from the dropping funnel. After the $COCl_2$ solution was completely added, 37g (0.25 mole) of cinnamic acid was added, followed by 1.5 liters of dichloromethane ($CH_2Cl_2$), after which 45g (0.25 mole) of theophylline was added. Next, pyridine (40g, 0.5 mole) in 100 ml of dichloromethane was added. The solution was heated under reflux for 20 hours. The crystals were filtered to give 85% yield of desired product.

(II) 18g theophylline (0.1 mole) was suspended in about 500 ml of chloroform or methylene chloride with 20 ml of N,N-dimethylformamide and 10 ml (0.12M) of pyridine. Next, 20g (0.12M) of cinnamoyl chloride in 100 ml of chloroform was added slowly to the reaction mixture. The solution was heated under reflux for 3–4 hours. The mixture was filtered while it was hot. When the filtrate was cooled, it gave the desired product. Some more desired product can also be recovered from the mother liquid. The reaction gave the final product in essentially quantitative yield. (90%) M.P. 235°.

Prior to initiation of the stability study, all samples were analyzed by elemental analysis, IR and UV to make sure that they were pure. Samples were then put into suitable vials and stored at specific conditions. At certain time intervals, the samples were weighed out and dissolved in anhydrous methylene chloride. The UV spectrum of each solution was taken. From the UV absorption, the percent of original compound remaining in each sample was calculated. All results attained are set out below in Table I.

TABLE I

| | | PERCENT OF ORIGINAL COMPOUND REMAINING | | | | | | | | | | | | | | | |
|---|---|---|---|---|---|---|---|---|---|---|---|---|---|---|---|---|---|
| | | | Weeks→ | | | | | | | | | | | | | | |
| Batch No. | Conditions | To | 1 | 2 | 3 | 4 | 5 | 6 | 7 | 8 | 9 | 10 | 11 | 12 | 13 | 14 15 | 2 yrs. |
| k-127 | 52% R.H. | 100 | 97 | 99 | 95 | 100 | 95 | 87 | 94 | 93 | 96 | 96 | — | 96 | — | 98 | 100 |
| 7-(3-phenyl- | 92% R.H. | 100 | 97 | 100 | 93 | 100 | 93 | 88 | 94 | 94 | 96 | 96 | — | 97 | — | 97 | 100 |
| propenoyl)- | 40° C | 100 | 100 | 100 | 100 | — | 93 | 99 | 99 | 100 | 100 | 100 | — | 100 | — | 100 | 100 |
| theophylline | 50° C | 100 | 100 | 96 | 100 | 100 | 98 | 89 | 97 | 97 | 100 | 100 | — | 100 | — | 100 | 100 |
| | 60° C | 100 | 100 | 100 | 98 | 100 | 99 | 90 | 96 | 96 | 98 | 100 | — | 100 | — | 97 | 100 |
| k-152 | 52% R.H. | 100 | 100 | — | 96 | 93 | 89 | 90 | 87 | 86 | 83 | 80 | 80 | | | | |
| 7,7'-succinyl- | 92% R.H. | 100 | 100 | — | 96 | 95 | 92 | 95 | 94 | 91 | 89 | 88 | 84 | | | | |
| ditheophylline | 40° C | 100 | 100 | — | 93 | 87 | 85 | 81 | 81 | 77 | 77 | 73 | — | | | | |
| | 50° C | 100 | 100 | — | 92 | 85 | 83 | 81 | 79 | 76 | 74 | 72 | — | | | | |
| | 60° C | 100 | 94 | — | 84 | 78 | 74 | 71 | 68 | 62 | 64 | 62 | — | | | | |

By substituting the remaining derivatives of this invention in the stability comparison described above, similar stability data is obtained.

The data presented above overwhelmingly demonstrates the unique stability characteristics of the compounds of the present invention over the prior art candidate compounds.

The pro-drug forms of this invention are suitably administered in oral dosage form, such as by tablet or capsule, by combining the same in a therapeutic amount with any oral pharmaceutically acceptable inert carrier, such as lactose, starch (pharmaceutical grade), dicalcium phosphate, calcium sulfate, Kaolin, Mannitol, and powdered sugar. In addition, when required, suitable binders, lubricants, disintegrating agents, and coloring agents can also be added. Typical binders include starch, gelatin, sugars, such as sucrose, molasses, and lactose, natural and synthetic gums such as acacia, sodium alginate, extract of Irish moss, carboxymethyl cellulose, methylcellulose, and polyvinylpyrrolidone, polyethylene glycol, ethylcellulose and waxes. Typical lubricants for use in these dosage forms can include, without limitation, boric acid, sodium benzoate, sodium acetate, sodium chloride, leucine, and polyethylene glycol. Suitable disintegrators can include, without limitation, starch, methylcellulose, agar, bentonite, cellulose and wood products, alginic acid, guar gum, citris pulp, carboxymethylcellulose, and sodium lauryl sulfate. If desired, a conventionally pharmaceutically acceptable dye can be incorporated into the dosage unit form, i.e., any of the standard FD&C dyes.

Any skilled artisan can prepare these oral dosage forms by simply referring to the oral dosage form preparatory procedure outlined in "REMINGTON'S PHARMACEUTICAL SCIENCES," Fourteenth Edition (1970), pages 1659 through 1698 inclusive.

While the therapeutic dosage range for the compounds of this invention will vary with the size and needs of the patient, generally speaking, therapeusis on a daily basis is achieved by administering 10 mg. to 15 mg. per Kg. of body weight, about every 8 to 12 hours.

From the foregoing description, one skilled in the art can easily ascertain the essential characteristics of this invention, and without departing from the spirit and scope thereof, can make varous changes and/or modifications to the invention for adapting it to various usages and conditions. As such, such changes and modifications are properly, equitably and intended to be, within the full range of equivalence of the following claims.

What we claim is:

1. A pro-theophylline compound of the formula:

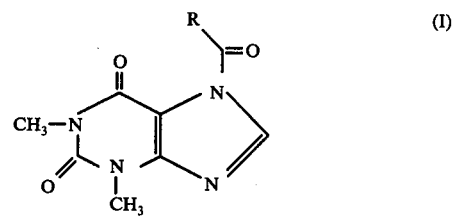

wherein R represents a straight or branched phenylalkenyl group having 2–8 carbon atoms in the alkenyl portion.

2. The compound of claim 1:
7-(3-phenyl-propenoyl)-theophylline
3. The compound of claim 1:
7-(6-phenyl-hexen-2-oyl)-theophylline
4. The compound of claim 1:
7-(8-phenyl-octen-5-oyl)-theophylline
5. A method for inducing a non-toxic, sustained therapeuticcally effective release of theophylline in the bloodstream of a warm-blooded animal which comprises:
orally administering thereto, a pharmaceutically effective amount of the compound of claim 1.
6. The method of claim 5, wherein said compound is:
7-(3-phenyl-propenoyl)-theophylline.
7. A pharmaceutical composition which comprises:
(1) a pharmaceutically effective amount of the compound of claim 1 in combination with,
(2) a pharmaceutically acceptable inert diluent.
8. A composition of claim 7, wherein said compound is:
7-(3-phenyl-propenoyl)-theophylline.

* * * * *